United States Patent
Tanida et al.

(10) Patent No.: US 6,794,367 B1
(45) Date of Patent: Sep. 21, 2004

(54) SOLID PREPARATIONS FOR ORAL ADMINISTRATION OF DRUGS RELATING TO GENES

(75) Inventors: Norifumi Tanida, Ibaraki (JP); Takeshi Goto, Ibaraki (JP); Jun Aoki, Ibaraki (JP)

(73) Assignee: Hisamitsu Pharmaceutical, Inc., Tosu (JP)

(*) Notice: Subject to any disclaimer, the term of this patent is extended or adjusted under 35 U.S.C. 154(b) by 0 days.

(21) Appl. No.: 09/700,817

(22) PCT Filed: May 17, 1999

(86) PCT No.: PCT/JP99/02546

§ 371 (c)(1),
(2), (4) Date: Nov. 20, 2000

(87) PCT Pub. No.: WO99/59639

PCT Pub. Date: Nov. 25, 1999

(30) Foreign Application Priority Data

May 19, 1998 (JP) .......................... 10-153912

(51) Int. Cl.⁷ .............................. A01N 43/04
(52) U.S. Cl. .................. 514/44; 424/479; 424/480; 424/482; 424/493; 424/494; 424/497; 536/23.1; 536/24.5; 435/320.1
(58) Field of Search .................. 514/44; 424/479, 424/480, 482, 493, 494, 497; 536/23.1, 24.5; 435/320.1

(56) References Cited

U.S. PATENT DOCUMENTS

| | | | |
|---|---|---|---|
| 5,614,503 A | | 3/1997 | Chaudhary et al. |
| 5,654,004 A | * | 8/1997 | Okayama .................... 424/479 |
| 5,714,679 A | | 2/1998 | Nichols et al. |
| 5,736,388 A | * | 4/1998 | Chada et al. ............ 435/320.1 |
| 5,834,186 A | | 11/1998 | George et al. |
| 5,854,038 A | | 12/1998 | Sullenger et al. |
| 5,874,415 A | * | 2/1999 | Kufe .......................... 514/44 |
| 6,096,722 A | * | 8/2000 | Bennett ...................... 514/44 |
| 6,151,525 A | * | 11/2000 | Soykan ........................ 607/50 |
| 6,180,621 B1 | * | 1/2001 | Kawamoto .................. 514/210 |
| 6,214,378 B1 | * | 4/2001 | Tanida ........................ 424/463 |
| 6,586,004 B2 | * | 7/2003 | Shimuzu ..................... 424/464 |

FOREIGN PATENT DOCUMENTS

| | | |
|---|---|---|
| EP | 0 383 526 A2 | 2/1990 |
| JP | 6-510665 | 12/1994 |
| JP | 8-505872 | 6/1996 |
| JP | 8-50723 | 8/1996 |
| JP | 9-505084 | 5/1997 |
| JP | 9-176038 | 7/1997 |
| JP | 9-507387 | 7/1997 |
| JP | 10004973 A | 1/1998 |
| WO | WO 93/03769 | 3/1993 |
| WO | WO 94/10983 | 5/1994 |
| WO | WO 97/10334 | 3/1997 |
| WO | WO 98/11779 | 3/1998 |

OTHER PUBLICATIONS

Steadman's Medical Dictionary (24th Edition, 1982), p. 522.*
Rossi et al (Methods: A Companion to Methods in Enzymology 5:1–5, 1993).*

* cited by examiner

*Primary Examiner*—Dave T. Nguyen
*Assistant Examiner*—Richard Schnizer
(74) *Attorney, Agent, or Firm*—Wolf, Greenfield & Sacks, P.C.

(57) ABSTRACT

The invention provides solid preparations for oral administration of gene-related drugs comprising a core containing the gene-related drug with a coating which does not disintegrated in small intestines, wherein said preparations can be easily tabletted, remain stable during the preparation process and said drug can be efficiently absorbed in digestive tracts.

16 Claims, No Drawings

SOLID PREPARATIONS FOR ORAL ADMINISTRATION OF DRUGS RELATING TO GENES

RELATED APPLICATIONS

This application claims the benefit under 35 U.S.C. §365 (c) of PCT International application PCT/JP99/02546, designating the United States of America, and filed May 17, 1999. This application is a national stage filing under 35 U.S.C. §371 of PCT application PCT/JP99/02546.

Foreign priority benefits are claimed under 35 U.S.C. §119(a)–(d) or 35 U.S.C. §365(b) of Japan application number 10-153912, filed May 19, 1998, which designated at least one country other than the United States.

TECHNICAL FIELD

The invention relates to a solid preparation for oral administration of gene-related drugs.

A variety of gene-related drugs have been developed as useful pharmaceuticals, though in the case of producing them as a solid preparation for oral administration, there are problems such as that worsened fluidity of mixed powder due to wettability of a gene-related drug and viscosity after its moisture absorption causing a compressing problem, in the case of increase of the mixed amount, production of tablets with good disintegration becomes difficult, and, in addition that it is very difficult to keep stability of a gene-related drug during a production process. Furthermore, even if a solid preparation for oral administration can be produced, a gene-related drug is easily decomposed in digestive tracts due to the unusually high instability in it, and so on, therefore, it has been generally considered difficult to develop a solid preparation appropriate for oral administration.

BACKGROUND ART

On the other hand, in the development of a general solid preparation for oral administration, recently various attempts have been made to make a drug which easily loses its due to decomposition in small intestines to be absorbed in large intestines in which the enzyme activity of protein decomposition is remarkably low by delivering it to the organ. Illustrative of such examples are oral preparations by the inventors (International application WO, 94/10983, A) mainly for drugs of protein or polypeptide nature having a high specificity toward lower digestive tracts such as large intestines. However, as to a gene-related drug, a solid preparation for oral administration which is practical and effective has not been developed yet owing to the above reasons.

SUMMARY OF THE INVENTION

Consequently, the problem of the invention is to solve problems in the prior art described above in a gene-related drug and to provide a solid preparation for oral administration which is practical and effective. More specifically, it is to provide a solid preparation for oral administration of a gene-related drug in which compressing preparation is easy, preparation processes are stable, and it is effectively absorbed in the digestive tracts.

The inventors made extensive researches to solve the above problems and found out that the decomposition activity for a gene-related drug, as for drugs of peptide nature is remarkably low in large intestines compared with small intestines, and as the result of continuing further research based on such evidence the inventors accomplished the invention.

Namely, the invention relates to a solid preparation with a coating around the core containing a gene-related drug for oral administration with releasability in lower digestive tracts in small intestines is applied.

The invention also relates to a solid preparation for oral administration in which the core is formed by compressing mixed powder of a gene-related drug and additives appropriately containing a binder, a saccharide, a disintegrator, an excipient or the like, and its outside is coated with an inner layer comprising a cationic copolymer and with an outer layer comprising an anionic copolymer.

Further, the invention comprises the following embodiments.

The above solid preparation for oral administration wherein the mixed ratio of a gene-related drug and a binder is 1:0.2–1:5 or the mixed ratio of a gene-related drug, a binder and an excipient is 1:0.2:0.01–1:5:1.

The above solid preparation for oral administration wherein the mixed ratio of a saccharide contained in the core containing a gene-related drug is in the range of 20–60 wt. %.

The above solid preparation for oral administration wherein a disintegrator contained in the core containing a gene-related drug is in the range of 2–15 wt. %.

The above solid preparation for oral administration, characterized in that a disintegrator is mixed in the ratio of 1:0.05–1:10 against the mixed amount of a gene-related drug and produced.

The above solid preparation for oral administration wherein an excipient contained in the core containing a gene-related drug is in the range of 0.1–15 wt. %.

The above solid preparation for oral administration wherein a gene-related drug contained in the core of the gene-related drug is in the range of 0.1–50 wt. %.

The above solid preparation for oral administration wherein a binder contained in the core containing a gene-related drug is in the range of 5–40 wt. %.

The above solid preparations for oral administration wherein the disintegrators are crospovidone, alpha starch, sodium carboxymethyl starch, carmellose, calcium carmellose, sodium carmellose, agar powder, sodium croscarmellose, crystalline cellulose, low substituted hydroxypropyl cellulose, starch, dextrin, hydroxyethylmethyl cellulose, hydroxypropyl starch, hydroxypropyl cellulose, hydroxypropylmethyl cellulose, polyvinylpyrrolidone, macrogol and mannitol.

The above solid preparations for oral administration wherein the saccharide are monosaccharides and disaccharides such as lactose, fructose, sucrose, glucose, xylitol, maltose, mannitol and sorbitol, or polysaccharides and derivatives thereof such as cellulose, crystalline cellulose, hydroxypropyl cellulose, hydroxyethylmethyl cellulose, ethyl cellulose, starch, dextrin, dextran, pectin and pullulan.

The above solid preparations for oral administration wherein the excipients are light anhydrous silicic acid, ethyl cellulose, carmelose, agar, magnesium aluminosilicate, calcium silicate, magnesium silicate, cyclodextrin, starch, synthetic aluminum silicate, synthetic hydrotalcite, titanium oxide, zinc oxide, magnesium oxide, alumina magnesium hydroxide, magnesium stearate, calcium stearate, aluminum silicate, talc, crystalline cellulose and lactose.

The above solid preparations for oral administration wherein the gene-related drugs are DNA, RNA and modified compounds thereof, and compounds thereof conjugated or bound to a carrier.

The above solid preparations for oral administration wherein the binders are crystalline cellulose, gumarabic, sodium alginate, ethyl cellulose, agar, carboxyvinyl polymer, carmelose, gelatin, low substituted hydroxypropyl cellulose, starch, dextrin, hydroxypropyl cellulose, hydroxypropylmethyl cellulose, pectin, polyvinylpyrrolidone, macrogol and methyl cellulose.

The above solid preparations for oral administration wherein the carriers comprise a cationic polymer, cationic lipid, virus vector and phage.

The above solid preparations for oral administration wherein the gene-related drugs comprise a nucleic acid, oligonucleotide, antisense, triple helix forming oligonucleotide (TFO), ribozyme, decoy, plasmid, cosmid, P1 phage, YAC (yeast artificial chromosome), chromosome, aptamer and phage.

Thus, the above problems were solved once for all by the solid preparations for oral administration of the invention.

DETAILED DESCRIPTION OF THE PREFERRED EMBODIMENTS

In the invention, illustrative of available gene-related drugs are DNA, RNA and modified compounds thereof, and compounds thereof conjugated or bound to a carrier, nucleic acid, oligonucleotide, antisense, triple helix forming oligonucleotide (TFO), ribozyme, decoy and plasmid. Illustrative of the carriers used are cationic polymer, cationic lipid, virus vector and phage.

Specifically, in the case of aiming at the colitis therapy as a topical therapeutic use are illustrated suppressive type gene pharmaceuticals such as TNF-α (Tumor necrosis factor α), ICAM-1 (Intercellular adhesion molecule-1), COX-2 (Cyclooxygenase-2), IL-1 (Interleukin-1), IL-6 (Interleukin-6) and IL-8 (Interleukin-8), or expression type gene pharmaceuticals such as IL-2 (Interleukin-2) and IL-10 (Interleukin-10). In the case of aiming at the colon cancer are illustrated suppressive type gene pharmaceuticals such as ICAM-1, COX-2 and TGF-β (Transforming growth factor β), or expression type gene pharmaceuticals such as INF-γ (Interferon-γ), TNF-α, APC (*Adenomatous Polyposis Coli*), p53, MCC (Mutated in Colorectal Carcinoma) and DCC (deleted in colorectal carcinomas). Further, in the case of aiming at the systemic diseases are illustrated suppressive type gene pharmaceuticals such as TNF-α, ICAM-1, COX-2, IL-1, IL-6, HIV (human immunodeficiency virus), bile acid transporter and each transporter of the small intestine, or expression type gene pharmaceuticals such as INF-γ, TNF-α, G-CSF (Granulocyte colony-stimulating factor), GM-CSF (Granulocyte macrophage colony-stimulating factor), glucose transporter, LHRH (Luteinizing hormone-releasing hormone) and calcitonin.

Also, in the invention, as to the above additives, an appropriate material and an appropriate mixed amount are selected by considering the fluidity of mixed powder, the disintegration of tablets, and the stability at the time of production.

In the following, the embodiments of the preparations are explained according to the method of production, the invention however, is not limited in any way by these.

First, the gene-related drug and the binder, or the gene-related drug, the binder and the excipient are mixed and ground using an appropriate micro-smasher such as an agate mortar, jet mill, pin mill or ball mill.

Here, illustrative of the available binders are crystalline cellulose, gum arabic, sodium alginate, ethyl cellulose, agar, carboxyvinyl polymer, carmelose, gelatin, low substituted hydroxypropyl cellulose (trade name; L-HPC, Shinnetsu Kagaku Kogyo Co., Ltd.), starch, dextrin, hydroxypropyl cellulose, hydroxypropylmethyl cellulose, pectin, polyvinylpyrrolidone, macrogol and methyl cellulose. Preferably crystalline cellulose is used.

Further, illustrative of the excipients are light anhydrous silicic acid, ethyl cellulose, carmellose, agar, magnesium silicate aluminate, calcium silicate, magnesium silicate, cyclodextrin, starch, synthetic aluminum silicate, synthetic hydrotalcite, titanium oxide, zinc oxide, magnesium oxide, alumina magnesium hydroxide (aluminum magnesium hydroxide), magnesium stearate, calcium stearate, aluminum silicate, talc, crystalline cellulose and lactose. Preferably light anhydrous silicic acid is used.

The mixed ratio of the binder contained in the core containing the gene-related drug is 5–40 wt. %., preferably 10–25 wt. %., likewise the mixed ratio of the excipient is 0.1–15 wt. %., preferably 1–5 wt. %., furthermore likewise the mixed ratio of the gene-related drug is 0.1–50 wt. %., preferably 5–30 wt. %.

On the other hand, the mixed ratio of the gene-related drug and the binder is in a preferable range for the fluidity of the mixed powder, the disintegration of tablets and the compressibility, specifically 1:0.2–1:5, preferably: 1:0.5–1:2. From the same standpoint, the mixed ratio of the gene-related drug, the binder and the excipient is 1:0.2:0.01–1:5:1, preferably 1:0.5:0.02–1:2:0,05.

Subsequently, the saccharide and the disintegrator is added to the obtained mix-ground product and mixed. Magnesium stearate is added to the mixture, and compressed with an appropriate tablet machine.

Here, illustrative of the saccharide are monosaccharides and disaccharides such as lactose, fructose, sucrose, glucose, xylitol, maltose, mannitol and sorbitol, or polysaccharides and derivatives thereof such as cellulose, crystalline cellulose, hydroxypropyl cellulose, hydroxyethylmethyl cellulose, ethyl cellulose, starch, dextrin, dextran, pectin and pullulan. Preferably lactose is used.

Here, illustrative of the disintegrators are crospovidone, alpha starch, sodium carboxymethyl starch, carmellose, calcium carmellose, sodium carmellose, agar powder, sodium croscarmellose, crystalline cellulose, low substituted hydroxypropyl cellulose (trade name; L-HPC, Shinnetsu Kagaku Kogyo Co., Ltd.), starch, dextrin, hydroxyethylmethyl cellulose, hydroxypropyl starch, hydroxypropyl cellulose, hydroxypropylmethyl cellulose, polyvinylpyrrolidone, macrogol and mannitol. Preferably crospovidone is used.

The mixed ratio of the excipient contained in the core containing the gene-related drug is 2–25 wt. %., preferably 5–15 wt. %., likewise the mixed ratio of the sugar is 20–60 wt. %., preferably 30–50 wt. %. The mixed ratio of the disintegrator against the mixed amount of the gene-related drug is in the range preferable for having a suitable disintegration in order to be delivered to the target site in the digestive tracts and for the compressibility, specifically in the ratio of 1:0.05–1:10, preferably 1:0.1–1:5. The mixed ratio of crospovidone as the disintegrator is in the range of 2.5–20 wt. %., preferably 5–15 wt. %.

Subsequently, the surface of the obtained uncoated tablet (core) is coated with the cationic copolymer and further with the anionic copolymer. As to the coating, coating solution is continuously applied by spraying under the condition that said core is kept at 30–50° C. The weight increase due to the cationic copolymer and the anionic copolymer is 5–15 wt. % based on the weight of the uncoated tablet, preferably 6–8 wt. %.

The cationic copolymer used as the inner layer has properties to be soluble or swelling at pH of 6.0 or below. Famous polymers include aminoalkyl methacrylate copolymer, a general name [copolymer comprising methyl methacrylate, butyl methacrylate and dimethylaminomethyl methacrylate, trade name: Eudragit E, manufactured by Röhm Co., Ltd.] or polyvinyl acetal diethylaminoacetate (trade name: AEA, manufactured by Sankyo Co., Ltd.). This polymer layer (inner layer) is formed by the use of membrane having the thickness of 10–300 μm and 1–40 wt. % of said solid drug weight, and regulated so as to release the active substance from said solid drug quickly when the pH condition of 6.0 or below continues. As for this inner layer, a suitable plastisizer is preferably used to obtain smooth coating membrane. The plastisizer includes triacetin, citric acid ester and polyethylene glycol. Also, the binding inhibitor includes talc, titanium oxide, calcium phosphate, hydrophobic light anhydrous silicic acid, etc.

The anionic copolymer used as the outer layer has a property to be easily soluble at pH of 5.5 or above. Famous polymers include methacrylic acid copolymer L, a general name, (copolymer comprising methacrylic acid and methyl methacrylate, tradename: Eudragit L100, manufactured by Röhm Co., Ltd.), methacrylic acid copolymer S (copolymer comprising methacrylic acid and methyl methacrylate, trade name: Eudragit S, manufactured by Röhm Co., Ltd.), hydroxypropylmethyl cellulose acetate succinate, hydroxypropylmethyl cellulose phthalate, etc. Said polymer is used in 1–40 wt. % of said solid drug.

According to the preparations, the gene-related drug can be delivered to the lower digestive tracts which can absorb it maintaining its activity stable, in particular to large intestines specifically, and the preparations disintegrate quickly at the same time of their delivery, therefore, the gene-related drug, which is a pharmacologically active substance, is released without loss of its activity. Further, at the time of production, the fluidity of powder is not destroyed to make stable compressing of tablets possible, and furthermore the stability of the gene-related drug can sufficiently be guaranteed in the time of production.

EXAMPLE

In the following, the invention is explained more concretely by the examples. The invention is not limited to these examples in any way.

Example 1

<Preparation of TNF α antisense>

The antisense (thio DNA) of TNF α with the sequence 5'-ATC Atg CTT TCT gTg CTC AT-3' (SEQ ID 1) was synthesized using the reagents shown in the following Table 1 on a nucleotide synthesis machine of DNA Synthesizer Oligo Pilot II (Pharmacia).

TABLE 1

| Reagent | Valid term | Manufacturer | Lot No. | Amount used (ml) |
|---|---|---|---|---|
| Acetonitril | 96.09.16 | Pharmacia Biotech. | 55383 | 9130 |
| Detritylation | 96.09.17 | Pharmacia Biotech. | 53968 | 7125 |
| 0.1MT-amidite | 96.09.02 | Pharmacia Biotech. | 5111736061 | 70 |

TABLE 1-continued

| Reagent | Valid term | Manufacturer | Lot No. | Amount used (ml) |
|---|---|---|---|---|
| 01.MA*-amidite | 96.09.02 | Pharmacia Biotech. | 5071730051 | 27 |
| 0.1MC*-amidite | 96.09.02 | Pharmacia Biotech. | 5081732061 | 44 |
| 0.1MG*-amidite | 96.09.02 | Pharmacia Biotech. | 5111734061 | 27 |
| Capping A | 96.09.16 | Pharmacia Biotech. | 55371 | 233 |
| Capping B | 96.09.16 | Pharmacia Biotech. | 55914 | 233 |
| Oxidation | 96.09.16 | Pharmacia Biotech. | 30465 | 4 |
| Beaucage | 96.09.16 | Pharmacia Biotech. | 6049798021 | 460 |
| Tetrazole | 96.09.16 | Pharmacia Biotech. | 6042875041 | 621 |

The crude oligonucleotide obtained was subsequently separated and purified under the following conditions on FPLC System manufactured by Pharmacia. Finally, its purity was checked using HPLC to confirm that the TNF α antisense (thio DNA) of 100% purity was obtained.

<Preparation of TNF α antisense tablets>

The tablets containing the TNFα antisense produced by the above procedures were produced according to the following formulation in Table 2–1 and Table 2–2. First, the TNFA antisense and light anhydrous silicic acid, or the TNFA antisense, crystalline cellulose and light anhydrous silicic acid were mixed and ground using a grinding machine, subsequently added with lactose and crospovidone, mixed, finally added with magnesium stearate, and mixed. The mixture was compressed using a tablet machine to produce tablets having the diameter of 7 mm and the weight of 200 mg.

TABLE 2-1

|  | (1) | (2) | (3) | (4) |
|---|---|---|---|---|
| TNF α antisense | 25 | 25 | 25 | 25 |
| Crystalline cellulose | 21 | 20 | 20 | 20 |
| Lactose | 43 | 43 | 48 | 50.5 |
| crospovidone | 10 | 10 | 5 | 2.5 |
| Light anhydrous silicic acid | 0 | 1 | 1 | 1 |
| Magnesium stearate | 1 | 1 | 1 | 1 |

*Each figure in Table represents parts by weight

TABLE 2-2

|  | (5) | (6) | (7) | (8) |
|---|---|---|---|---|
| TNF α antisense | 25 | 25 | 25 | 25 |
| Crystalline cellulose | 21 | 41 | 11 | 5 |
| Lactose | 33 | 23 | 53 | 59 |
| crospovidone | 20 | 10 | 10 | 10 |
| Magnesium stearate | 1 | 1 | 1 | 1 |

*Each figure in Table represents parts by weight

The following coating was carried out on said cores obtained.

| | |
|---|---|
| Eudragit E | 7 pt. by wt. |
| Ethanol | 70 pt. by wt. |
| Water | 19.5 pt. by wt. |
| Talc | 3.5 pt. by wt. |

As to the inner layer, the above solution was continuously applied by spraying under the condition that said cores were kept at 50° C. The weight increase of said core was 14 mg per tablet. After spraying, said cores were dried and further applied with the following solution.

| | |
|---|---|
| Eudragit S | 7.0 pt. by wt. |
| Ethanol | 70.0 pt. by wt. |
| Water | 18.8 pt. by wt. |
| Talc | 3.5 pt. by wt. |
| Polyethylene glycol 600 | 0.7 pt. by wt. |

As to the outer layer, the above solution was continuously applied by spraying under the condition in which said cores were kept at 50° C. The weight increase of said core was 14 mg per tablet.

Comparative Example 1

<Preparation of TNF α antisense tablets>

The tablets containing the TNF α antisense were produced according to the following formulation. First, the TNF α antisense, crystalline cellulose and lactose were mixed in a vinyl bag. The mixture was added finally with magnesium stearate, mixed and compressed using a tablet machine to produce tablets having the diameter of 7 mm and the weight of 200 mg.

| | |
|---|---|
| TNF α antisense | 26.5 pt. by wt. |
| Crystalline cellulose | 21 pt. by wt. |
| Lactose | 51.5 pt. by wt. |
| Magnesium stearate | 1 pt. by wt. |

The following coating was carried out on said cores obtained.

| | |
|---|---|
| Eudragit E | 7 pt. by wt. |
| Ethanol | 70 pt. by wt. |
| Water | 19.5 pt. by wt. |
| Talc | 3.5 pt. by wt. |

As to the inner layer, the above solution was continuously applied by spraying under the condition in which said cores were kept at 50° C. The weight increase of said core was 14 mg per tablet. After spraying, said cores were dried and further applied with the following solution.

| | |
|---|---|
| Eudragit S | 7.0 pt. by wt. |
| Ethanol | 70.0 pt. by wt. |
| Water | 18.8 pt. by wt. |
| Talc | 3.5 pt. by wt. |
| Polyethylene glycol 600 | 0.7 pt. by wt. |

As to the outer layer, the above solution was continuously applied by spraying under the condition in which said cores were kept at 50° C. The weight increase of said core was 14 mg per tablet.

Comparative Example 2

<Preparation of TNF α antisense tablets>

The tablets containing the TNF α antisense were produced according to the following formulation. First, the TNF α antisense, crystalline cellulose, lactose and crospovidone were mixed in a vinyl bag. The mixture was added finally with magnesium stearate, mixed and compressed using a tablet machine to produce tablets having the diameter of 7 mm and the weight of 200 mg.

| | |
|---|---|
| TNF α antisense | 26.5 pt. by wt. |
| Crystalline cellulose | 21 pt. by wt. |
| Lactose | 41.5 pt. by wt. |
| Crospovidone | 10 pt. by wt. |
| Magnesium stearate | 1 pt. by wt. |

The following coating was carried out on said cores obtained.

| | |
|---|---|
| Eudragit E | 7 pt. by wt. |
| Ethanol | 70 pt. by wt. |
| Water | 19.5 pt. by wt. |
| Talc | 3.5 pt. by wt. |

As to the inner layer, the above solution was continuously applied by spraying under the condition in which said cores were kept at 50° C. The weight increase of said core was 14 mg per tablet. After spraying, said cores were dried and further applied with the following solution.

| | |
|---|---|
| Eudragit S | 7.0 pt. by wt. |
| Ethanol | 70.0 pt. by wt. |
| Water | 18.8 pt. by wt. |
| Talc | 3.5 pt. by wt. |
| Polyethylene glycol 600 | 0.7 pt. by wt. |

As to the outer layer, the above solution was continuously applied by spraying under the condition in which said cores were kept at 50° C. The weight increase of said core was 14 mg per tablet.

Test Example 1

The evaluation was made on the disintegration and the content uniformity of the tablets prepared in the Example 1 and the Comparative Examples 1 and 2, and on the fluidity of mixed powders in the production processes and the compressibility of powders. The evaluation was made on the fluidity of the powders by the deviation of the weight of uncoated tablets, on the compressibility by the hardness of uncoated tablets prepared at the compressing pressure of 2.0 tons or less, the adhesion of powders to the mortar and the mallet at the time of compressing or the cracking after capping, sticking, lamination and coating of tablets.

As to the content uniformity test, the test was carried out according to the test method described in the 13th Japanese Pharmacopoeia using 10 tablets. As to the disintegration test, the test was carried out under the following conditions using disintegrating machine of Japanese Pharmacopoeia.

Test Method for Disintegration Test:

About 1 L of buffer solution of pH 7.5 was added into a wall-thick beaker and placed in the water bath of a disintegration test machine, whereby water temperature was set at about 39° C. In each of six auxiliary cylinders installed in a basket one tablet was inserted, further an auxiliary plate was inserted on the tablet, and the basket was mounted to the hanging rod. After confirming that the water temperature of the buffer solution of pH 7.5 in the wall-thick beaker was kept at about 37° C., the test was started. The basket was moved up and down in the buffer solution of pH 7.5 for 4 hours and subsequently moved up and down in the buffer solution of pH 5.5. The time spend from the time of the transfer to the buffer solution of pH 5.5 until the tablet's disintegration was measured and recorded. The tablet was judged to have disintegrated when the powders inside the coating membrane disappeared and a part of the auxiliary plate touched the basket.

1. Preparation of Buffer Solution

Buffer Solution of pH 7.5:

Sodium chloride 63.09 g, sodium dihydrogenphosphate dihydrate 0.936 g and disodium hydrogenphosphate dodecahydrate 13.053 g were measured respectively, dissolved with addition of purified water and made to 6 L after being adjusted to pH 7.5.

Buffer Solution of pH 5.5:

Sodium chloride 63.09 g, 3.5 M aq. acetic acid solution 3.5 mL and 2 M sodium acetate solution 60 mL were measured respectively, dissolved with addition of purified water and made to 6 L after being adjusted to pH 5.5.

The test results are shown in Table 3;

1. Mixing Effect of a Disintegrator (Crospovidone):

Comparing the disintegration of the preparation of the comparative example 1 prepared without mixing crospovidone with that of the preparation of the Example 1-(1) mixed with crospovidone, the disintegration of the preparation of the Comparative Example 1 was extremely bad; on the contrary the preparation of the Example 1-(1) showed good disintegration.

2. Effect of Mixed and Grinding:

Comparing the fluidity of the mixed powders before compressing in the preparation of the Example 1-(1) in which the mixed grinding was made in the production process with that in the preparation of the Comparative Example 2 of the same formulation in which the mixed grinding was not made, the fluidity was extremely low in the Comparative Example 2 in which the mixed grinding was not made; on the contrary the Example 1-(1) showed a good fluidity.

3. Examination of the Mixed Ratio of a Disintegrator (Crospovidone):

Comparing the disintegration of the tablets of the Examples 1-(1), (2), (3), (4) and (5) formulated with mixed amounts of crospovidone 5–10 wt. %, in the mixed amount of less than 10 wt. %, the disintegration was in the range of acceptance, but it was a little bad; that of the mixed amount of 10 wt. % showed the most suitable disintegration time. Further, in the mixed amount of 20 wt. % (the Example 1-(5)) the compressibility was bad, and there was a tendency that disintegration was conversely too speedy.

4. Examination of the Mixed Ratio of a Binder (Crystalline Cellulose):

Comparing the fluidity and the compressibility of the tablets of the examples 1-(1), (6), (7), and (8) formulated with a mixed amount of crystalline cellulose 5–41 wt. %, in 5 wt. % the fluidity was a little bad and there was also a problem in compressibility. That showing the most suitable fluidity and compressibility was the formulation of 20 wt. % (Example 1-(1)). In the formulation (tablet (6)) in which the mixed amount of crystalline cellulose was increased to 40 wt. %, there was a tendency that the compressibility got worse.

TABLE 3

| | Tablet No. | Fluidity | Compressibility | Disintegration | Content uniformity test result |
|---|---|---|---|---|---|
| Example 1 | (1) | ○ | ○ | ○ | ○ |
| | (2) | ○ | ○ | Δ | ○ |
| | (3) | ○ | ○ | Δ | ○ |
| | (4) | ○ | ○ | X | ○ |
| | (5) | ○ | X | X | — |
| | (6) | ○ | Δ | ○ | ○ |
| | (7) | Δ | Δ | — | — |
| | (8) | X | X | — | — |
| Comparative Example 1 | | X | X | X | X |
| Comparative Example 2 | | X | X | Δ | X |

*○: Good,
Δ: Within the range of acceptance, but a little problematic,
X: Problematic,
—: Not evaluated

What is claimed is:

1. A solid preparation with a coating around a core containing a nucleic acid drug for oral administration that provides releasability of the nucleic acid drug in lower digestive tracts, wherein the coating does not disintegrate in the small intestines, wherein the coating has a double-coated structure of an inner layer comprising a cationic copolymer and an outer layer comprising an anionic copolymer, wherein the core containing the nucleic acid drug contains a binder as an additive, and the mixed ratio of the nucleic acid drug and the binder is in the range of 1:0.2 to 1:5 (w/w) therefor.

2. The solid preparation for oral administration according to claim 1 wherein the core containing the nucleic acid drug further contains an excipient as an additive, and the mixed ratio of the nucleic acid drug, the binder and the excipient is in the range of 1:0.2:0.01 to 1:5:1 (w/w) therefor.

3. The solid preparation for oral administration according to claims 1 or 2 wherein the nucleic acid drug further contains one or both of a disintegrator and a saccharide as additives.

4. The solid preparation for oral administration according to claim 3 wherein the mixed ratio of the saccharide contained in the core containing the nucleic acid drug is in the range of 20–60 wt. %.

5. The solid preparation for oral administration according to claim 3 wherein the disintegrator contained in the core containing the nucleic acid drug is in the range of 2–15 wt. %.

6. The solid preparation for oral administration according to claim 3 wherein the disintegrator is mixed for production in a ratio in the range of 1:0.5 to 1:10 (w/w) against the content of the nucleic acid drug.

7. The solid preparation for oral administration according to claim 2 wherein the excipient contained in the core containing the nucleic acid drug is in the range of 0.1–15 wt. %.

8. The solid preparation for oral administration according to claim 1 wherein the nucleic acid drug contained in the core containing the nucleic acid drug is in the range of 0.1–50 wt. %.

9. The solid preparation for oral administration according to claim 1 wherein the binder contained in the core containing the nucleic acid drug is in the range of 5–40 wt. %.

10. The solid preparation for oral administration according to claim 3 wherein the disintegrator is selected from the group consisting of crospovidone, alpha starch, sodium carboxymethyl starch, carmellose, calcium carmellose, sodium carmellose, agar powder, sodium croscarmellose, crystalline cellulose, low substituted hydroxypropyl cellulose, starch, dextrin, hydroxyethylmethyl cellulose, hydroxypropylmethyl cellulose, polyvinylpyrrolidone, macrogol and mannitol.

11. The solid preparation for oral administration according to claim 3 wherein the saccharide is a monsaccharide or a disaccharide selected from the group consisting of lactose, fructose, sucrose, glucose xylitol, maltose, mannitol and sorbitol, or is a polysaccharide or derivative thereof such as cellulose, crystalline cellulose, hydroxypropyl cellulose, hydroxypropylmethyl cellulose, ethyl cellulose, starch, dextrin, dextran, pectin and pullulan.

12. The solid preparation for oral administration according to claim 2 wherein the excipient is selected from the group consisting of light anhydrous silicic acid, ethyl cellulose, carmellose, agar, magnesium aluminosilicate, calcium silicate, magnesium silicate, cyclodextrin, starch, synthetic aluminum silicate, synthetic hydrotalcite, titanium oxide, zinc oxide, magnesium oxide, alumina magnesium hydroxide, magnesium stearate, calcium stearate, aluminum silicate, talc, crystalline cellulose and lactose.

13. The solid preparation for oral administration according to claim 1 wherein the nucleic acid drug is selected from the group consisting of DNA, RNA, modified nucleic acids, or nucleic acids conjugated or bound to a carrier.

14. The solid preparation for oral administration according to claim 1 wherein the binder is selected from the group consisting of crystalline cellulose, gum arabic, sodium alginate, ethyl cellulose, agar, carboxyvinyl polymer, carmellose, gelatin, low substituted hydroxypropyl cellulose, starch, dextrin, hydroxypropyl cellulose, hydroxypropylmethyl cellulose, pectin, polyvinylpyrrolidone, macrogol and methyl cellulose.

15. The solid preparation for oral administration according to claim 13 wherein the carrier is selected from the group consisting of a cationic polymer, cationic lipid, virus vector and phage.

16. The solid preparation for oral administration according to claim 1 wherein the nucleic acid drug is one or more drugs selected from the group consisting of a nucleic acid, oligonucleotide, antisense, triple helix forming oligonucleotide (TFO), ribozyme, plasmid, cosmid, YAC (yeast artificial chromosome), aptamer and phage.

* * * * *

SEQUENCE LISTING

<160> NUMBER OF SEQ ID NOS: 1

<210> SEQ ID NO 1
<211> LENGTH: 20
<212> TYPE: DNA
<213> ORGANISM: Homo sapiens

<400> SEQUENCE: 1
atcatgcttt ctgtgctcat                    20